United States Patent
Chou et al.

(10) Patent No.: US 6,740,911 B1
(45) Date of Patent: May 25, 2004

(54) α-WO₃-GATE ISFET DEVICES AND METHOD OF MAKING THE SAME

(75) Inventors: Jung Chuan Chou, Yunlin (TW); Jung Lung Chiang, Changhua (TW)

(73) Assignee: National Yunlin University of Science and Technology, Yunlin (TW)

( * ) Notice: Subject to any disclaimer, the term of this patent is extended or adjusted under 35 U.S.C. 154(b) by 0 days.

(21) Appl. No.: 09/533,591

(22) Filed: Mar. 23, 2000

(30) Foreign Application Priority Data

Jun. 11, 1999 (TW) .................... 88109799 A

(51) Int. Cl.⁷ ............................... H01L 29/76
(52) U.S. Cl. ............ 257/288; 257/286; 257/257; 257/279; 257/253; 257/262; 257/252; 257/410; 257/411; 257/414
(58) Field of Search ................ 257/288, 286, 257/287, 249, 253, 262, 252, 410, 411, 414

(56) References Cited

U.S. PATENT DOCUMENTS

| | | | | |
|---|---|---|---|---|
| 4,502,938 A | * | 3/1985 | Covington et al. | 204/412 |
| 4,505,028 A | * | 3/1985 | Kobayashi et al. | 29/578 |
| 5,079,178 A | * | 1/1992 | Chouan et al. | 437/40 |
| 5,394,264 A | * | 2/1995 | Marchese et al. | 359/270 |
| 5,923,056 A | * | 7/1999 | Lee et al. | 257/192 |
| 6,121,094 A | * | 9/2000 | Gardner et al. | 438/287 |
| 6,236,075 B1 | * | 5/2001 | Hsiung et al. | 257/252 |
| 6,291,868 B1 | * | 9/2001 | Weimer et al. | 257/413 |
| 6,303,494 B1 | * | 10/2001 | Yeo et al. | 438/653 |

* cited by examiner

Primary Examiner—Tom Thomas
Assistant Examiner—Edgardo Ortiz
(74) Attorney, Agent, or Firm—International Property Solutions, Incorporated

(57) ABSTRACT

Disclosed is an ISFET comprising a H⁺-sensing membrane consisting of RF-sputtering a-WO₃. The a-WO₃/SiO₂-gate ISFET of the present invention is very sensitive in aqueous solution, and particularly in acidic aqueous solution. The sensitivity of the present ISFET ranges from 50 to 58 mV/pH. In addition, the disclosed ISFET has high linearity. Accordingly, the disclosed ISFET can be used to detect effluent.

11 Claims, 6 Drawing Sheets

α-WO₃-GATE ISFET DEVICES AND METHOD OF MAKING THE SAME

BACKGROUND OF THE INVENTION

1. Field of the Invention

The invention relates to an ion sensitive field effect transistor (ISFET), and in particular relates to an a-$WO_3$-gate ISFET fabricated by RF-sputtering for detecting the hydrogen ions in aqueous solution. In addition, this invention relates to a method for making the a-$WO_3$-gate ISFET.

2. Description of the Prior Art

The ISFET was first disclosed by P. Bergveld in 1970. The device is a product of applied electrochemistry and microelectronics, and has the function of ion selection and the properties of the FET. This ion sensitive device is strictly different from the traditional ion selection electrode. P. Bergveld disclosed a FET, wherein the metal film set in the gate of traditional FET was removed. Moreover, the device was dipped in electrolyte, wherein no reference electrode was present. However, it was found that a reference electrode must be added to determine the relative voltage between the electrolyte and the semiconductor substrate during detecting so that the ISFET can be operated correctly.

Currently, a large amount of researches on ISFETs are underway. One interesting filed of the research is the use of the membrane for detection. When single gate detecting membrane consists of silicon dioxide, the sensitivity and stability of the device are poor. However, when the detecting membrane of the ISFET consists of double dielectric layers, such as $Si_3N_4/SiO_2$, $Al_2O_3/SiO_2$, $Ta_2O_5/SiO_2$, $SnO_2/SiO_2$ and a-$WO_3/SiO_2$, the properties are superior to the ISFET with a detecting membrane comprising a single $SiO_2$ gate. Regarding a $H^+$-ISFET, it has been noted that a greater range of ions can be detected when a corresponding detecting membrane is covered on the $SiO_2$ or $Si_3N_4$ detecting membrane.

Today, the sorts of the FET based on ISFET process used to detect ions and chemicals have reached more than 30. Moreover, the shrinking, integration, and multi-functionization of the ISFET devices have greatly progressed.

The advantages of the ISFET can be summarized as follows:

1. Shrinkage size and micro-solution detectable;
2. High input resistance;
3. Low output resistance;
4. Fast reaction time;
5. Low price;
6. MOSFET processes compatible; and
7. Biosensor applicable.

Current ISFET researches can be classified into six categories:

1. Preparation of sensing membrane by CVD, thermal oxidation, Σ-gun evaporation, thermal evaporation and sputtering;
2. Shrinkage of the device and the reference electrode;
3. Basic theory, such as site binding model;
4. Packing technique, such as packing material, for example Si-rubber and epoxy;
5. Integration of the devices and circuits; and
6. Simulation of the ISFETs.

A number of patents relating to ISFETs have been obtained, as summarized hereinafter. U.S. Pat. No. 4,358,274 discloses a method and device for compensating temperature-dependent characteristics change in ion-sensitive FET transducer, which is characterized by using a differential system consisting of ISFETs and a circuits-readout module. U.S. Pat. No. 4,609,932 discloses a non-planar ion-sensitive field-effect transistor device, which is characterized by forming a 3-D ISFET device by laser drilling and solid-state diffusion. U.S. Pat. No. 4,657,658 discloses a semiconductor integrated circuit for sensing a physico-chemical property of an ambient and includes a pair of semiconductor devices having a similar geometric and physical structure, one device being sensitive to the property, the other being insensitive to the property, together with a differential amplifier having feedback connection to one of the pair of semiconductor devices. U.S. Pat. No. 4,812,220 discloses an enzyme sensor for determining a concentration of glutamate, comprising an immobilize enzyme acting specifically to a substrate and a transducer for converting the quantitive change of a substance or heat which is produced or consumed during an enzyme reaction to an electrical signal, wherein the enzyme is glutamine synthetase and the transducer is the pH glass electrode or ion-sensitive field-effect transistor (ISFET). The enzyme sensor can be miniaturized and can accurately determine a concentration of glutamate even when it is low. U.S. Pat. No. 4,839,000 discloses buffer compensation in enzyme-modified ion sensitive devices, which is characterized by using enzyme-modified ion sensitive field transistors to control the compensation of the ions in solution. U.S. Pat. No. 5,319,226 discloses a method of fabricating an ion sensitive field effect transistor with a $Ta_2O_5$ hydrogen ion sensing membrane, wherein a $Ta_2O_5/Si_3N_4/SiO_2$ dielectric layer, used as the sensor-device, is formed over the gate region of the ion sensitive field effect transistor by RF-sputtering. U.S. Pat. No. 5,350,701 discloses a process for producing a surface gate of an integrated electrochemical sensor, and the integrated chemical sensor thus produced, wherein the surface gate is particularly sensitive to alkaline-earth species, and more particularly, sensitive to the calcium ion. U.S. Pat. No. 5,387,328 discloses a bio-sensor using ion sensitive field effect transistor with platinum, wherein an immobilize enzyme membrane is immobilized on the ion-sensing film to determine the concentration of glucose. Moreover, a Pt reference electrode is introduced to shrink the size of the bio-sensor. U.S. Pat. No. 5,407,854 disclose the ESD protection of ISFET sensors, which is characterized by providing a method for providing electrostatic discharge protection to ion sensitive field effect transistor.

There has been interest in the material of the sensing membrane of ISFET, wherein a-$WO_3$ is a potential for use as the gate of the ISFET. The a-$WO_3$ is a N-type semiconductor compound, and has both wide energy gap (Eg= 2.1~3.8 eV) and high dielectric constant ($\epsilon$=260 $\epsilon_0$). Moreover, a-$WO_3$ is redox reversible, electrochromic and photochromic. Because the range of the resistivity of a-$WO_3$ is large (ranging from $10^{-3}$ to $10^{11}$ Ω·cm), the a-$WO_3$ has potential to be a sensor, such as a gas sensor for detecting the $CO_2$, $NO_2$, $H_2S$, and so on.

Currently, a $WO_3$ layer can be formed by E-bean evaporation, DC or AC sputtering, thermal evaporation, vacuum evaporation, and CVD. The composition of the $WO_3$ layer and its properties vary with the selected method and condition during preparing the $WO_3$ layer. Most of the $WO_3$ layers are amorphous, polycrystalline or crystalline. The composition and structure of the $WO_3$ layer will directly affect its resistivity and electrochromic property; thereby the properties of the devices are determined by the composition and structure of the $WO_3$ layer.

In general, the composition of the $WO_3$ layer is hard to control regardless of which method is used in its formation. For example, the composition of the $WO_3$ layer made by vacuum evaporation is hard to control and the surface of the $WO_3$ layer is not uniform.

Some patents about the usage of ISFET have been disclosed using a $H^+$-FET sensing film including $SiO_2$, $Si_3N_4$, $Al_2O_3$, and $Ta_2O_5$. However, a FET used to detect the industrial effluent is seldom mentioned, and especially a FET used to detect the effluent of low pH. Moreover, the gate of the conventional ISFET consists of a single $SiO_2$ layer; thereby the sensitivity and linearity cannot meet the practical requirements.

SUMMARY OF THE INVENTION

One feature of the invention discloses an ISFET comprising a $H^+$-sensing material consisting of a-$WO_3$. The present ISFET is very sensitive in solution, and particularly in acidic solution. The sensitivity of the ISFET of the present invention ranges from 50 to 58 mV/pH. In addition, the disclosed ISFET has high linearity. Accordingly, the ISFET of the present invention is suitable applied to detect effluent.

In order to achieve the above-mentioned feature, the present invention discloses a RF-sputtering a-$WO_3$ gate ISFET and the making thereof. This invention is characterized by forming the a-$WO_3$ layer as the sensing membrane of the ISFET by RF-sputtering, wherein the reactant consists of Ar and $O_2$. That is, the gate of the detecting device consists of a-$WO_3$ layer/$SiO_2$ layer. Comparing the sensitivity of the sensing membrane in aqueous solution with various pH values, the results indicate the device made according to this invention is sensitive to the acidic aqueous solution and has good linearity. Accordingly, the detecting device according to this invention is superior to the traditional detecting device containing a gate consisting of a single $SiO_2$ layer.

Other feature and advantages of the invention will be apparent from the following detailed description, and from the claims.

BRIEF DESCRIPTION OF THE DRAWINGS

The present invention will become more fully understood from the detailed description given hereinbelow and the accompanying drawings, given by way of illustration only and thus not intended to be limitative of the present invention.

DETAILED DESCRIPTION OF THE INVENTION

Figure 1A:
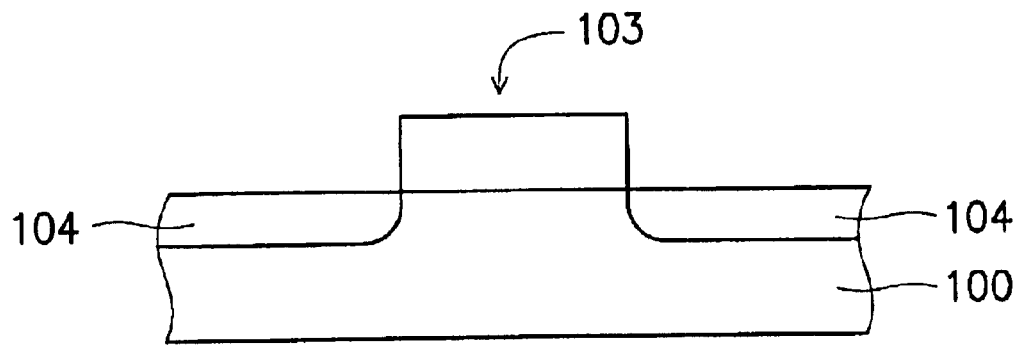
FIGS. 1a~1c are cross-sectional views of the processes according to the preferred embodiment of the invention.

The present invention provides an a-$WO_3$ gate ISFET device comprising: a semiconductor substrate; a gate oxide layer on the semiconductor substrate; an a-$WO_3$ layer overlying the gate oxide layer to form an a-$WO_3$ gate; a source/drain in the semiconductor substrate beside the a-$W_3$ gate; a metal wire on the source/drain; and a sealing layer overlying the metal wire, and exposing the a-$WO_3$ layer.

In an embodiment of the present invention, the length of the channel, the width of the channel and ratio of width/length of the channel of the ISFET are 50 $\mu$m, 1000 $\mu$m and 20, respectively. The semiconductor substrate is P-type with a resistivity ranging from 8 to 12 $\Omega\cdot$cm. Moreover, the lattice parameter of the semiconductor is (1, 0, 0). The thickness of the gate oxide is about 1000Å, and the thickness of the tungsten oxide layer is at least 1000Å. The metal wire consists of Al. The sealing layer consists of epoxide resin. The source/drain is N-type, which may consists of phosphorous.

The present invention also provides a method for fabricating an a-$WO_3$ gate ISFET device, comprising the following steps: providing a semiconductor substrate; forming an imaginary gate on the semiconductor substrate to define a gate area of the ISFET; forming a source/drain in the semiconductor substrate beside the imaginary gate; removing the imaginary gate; and forming an a-$WO_3$ gate in the gate area to form an ISFET.

In an embodiment of the present invention, the semiconductor substrate is P-type with a resistivity of the semiconductor substrate ranges from 8 to 12 $\Omega\cdot$cm. Moreover, the lattice parameter of the semiconductor is (1, 0, 0). The imaginary gate consists of silicon dioxide with a thickness about 5000Å. In addition, the imaginary gate is removed by wet-etching.

The step for forming an imaginary gate in the semiconductor gate to define a gate area of the ISFET, comprises: cleaning the semiconductor substrate; forming a pad oxide layer on the semiconductor substrate; and removing a portion of the pad oxide layer to form an imaginary gate to define the area of the gate.

In the above-mentioned step for forming an imaginary gate in the semiconductor gate, the pad oxide layer can be formed by wet-oxidation. Additionally, the step of removing a portion of the pad oxide layer can be completed by wet etching.

The step of forming a source/drain beside the imaginary gate comprises doping the semiconductor substrate by using the imaginary gate as a mask to form a source/drain, wherein the dose of the dopants is about $10^{15}$ atoms/cm$^2$.

The step of forming an amorphous tungsten oxide gate in the gate area comprises: forming a gate oxide layer on the gate area, and forming an amorphous tungsten oxide layer to form the amorphous tungsten oxide gate, wherein the gate oxide consists of silicon oxide with a thickness of about 1000Å. In addition, the amorphous tungsten oxide gate is formed by RF-sputtering.

The present invention also provides a method for fabricating an a-$WO_3$ gate ISFET device, comprising following steps: providing a P-type semiconductor substrate; forming a pad oxide layer on the semiconductor layer; removing a portion of the pad oxide layer to form an imaginary gate to define a gate area; doping the semiconductor substrate using the imaginary gate as a mask to form a source/drain beside the imaginary gate; removing the imaginary gate; forming a gate oxide layer on the semiconductor substrate; and forming an a-WO$_3$ layer on the gate oxide layer to form an a-WO$_3$ gate.

In an embodiment of the above method, the resistivity of the semiconductor substrate ranges from 8 to 12 Ω·cm and the lattice parameter of the semiconductor is (1, 0, 0). The thickness of the imaginary gate is about 5000Å. The pad oxide layer is formed by wet oxidation. The step of partially removing the pad oxide layer is performed by wet etching. The dopants used to dope the semiconductor substrate to form a source/drain beside the imaginary gate consist of phosphorous with a dosage of about $10^{15}$ atoms/cm$^2$. The imaginary gate is removed by wet etching. The gate oxide layer consists of silicon dioxide with a thickness of about 1000Å. The a-WO$_3$, layer is formed by RF-sputtering.

EMBODIMENT OF THE INVENTION

Figure 1B:
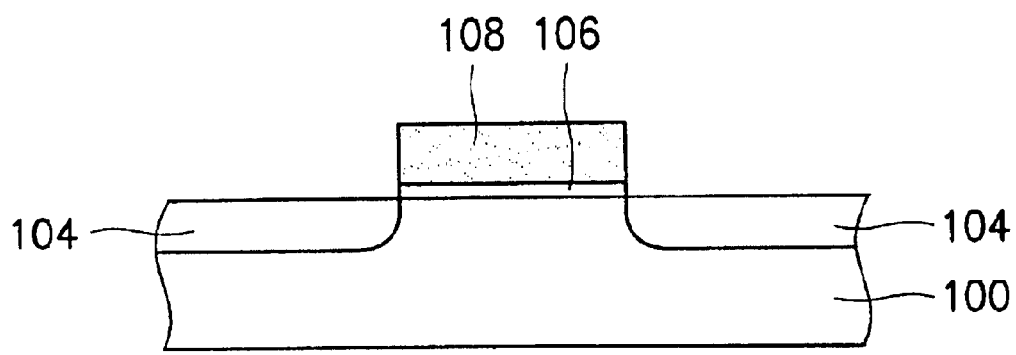

The ion sensitive field effect transistor (ISFET) according to the embodiment of this invention is illustrated in FIGS. 1a~1b.

Referring to FIG. 1a, a P-type (1, 0, 0) semiconductor substrate 100 with a resistivity ranging from 8 to 12 Ω·cm was provided. A pad oxide layer 102 consisting of silicon dioxide with a thickness of 5000Å was formed on the substrate 100 by wet-oxidation. A first photoresist pattern (non-shown) was formed on the pad oxide layer 102 by conventional photolithography. Using the photoresist pattern as a mask, a dummy gate 103 used to define the subsequent gate area was formed by removing a portion of the pad oxide layer 102.

Then, using the dummy gate 103 as a mask, impurities were implanted into the semiconductor substrate to form a source/drain 104 beside the dummy gate 103. The impurities implanted herein were boron ions with a dose of $10^{15}$ cm$^{-2}$.

Referring to FIG. 1b, the dummy gate 103 was removed, that is the pad oxide layer 102 and the first photoresist pattern were removed by wet-etching. An insulating layer 106 consisting of silicon dioxide with a thickness of about 1000Å was formed on the semiconductor substrate 100. A second photoresist pattern (non-shown) was formed on the insulating layer 106 by photolithography. Then, using the second photoresist pattern as a mask, the insulating layer 106 outside the gate area was removed. The residual insulating layer within the gate area was used as a gate oxide layer. Subsequently, the second photoresist layer was removed.

An amorphous tungsten oxide layer 108 was formed on the insulating layer 106 by RF-sputtering. An amorphous tungsten oxide layer 108 with a thickness of at least 1000Å was sputtered on the insulating layer 106. Then a gate 109 consisting of the gate oxide layer 106 and the a-WO$_3$ layer 108 was generated. Thus, an a-WO$_3$ ISFET was obtained. The a-WO$_3$ ISFET had a channel length of about 50 μm and a channel width of about 1000 μm. Thus, the aspect ratio (i.e. channel width/channel length) of the present a-WO$_3$ ISFET was 20.

Figure 1C:
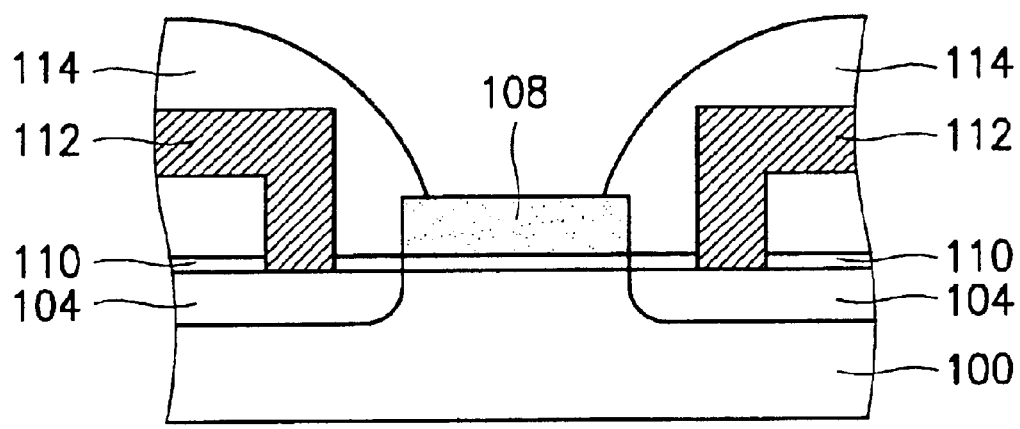

Referring to FIG. 1c, an interconnecting process was performed to obtain circuits of the ion sensitive field effect transistor (ISFET) using traditional interconnect steps for MOS. Therefore, an insulating layer 110 was formed on the source/drain 104, and a metal wire 112 was formed on the insulating layer 110 by etching and sputtering. Finally, a sealing layer 114 consisting of insulator was formed to seal the metal wire 112 except the amorphous tungsten oxide layer 108. The metal wire 112 consisted of aluminum, and the sealing layer 114 consists of epoxide resin.

Figure 2:
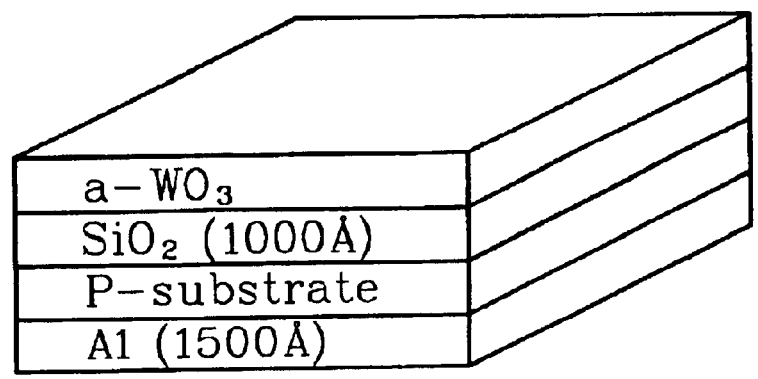
FIG. 2 shows the EIS structure consisting of a-$WO_3$/$SiO_2$.

FIG. 2 shows the scheme of the RF-sputtering a-WO$_3$/SiO$_2$ gated Electrolyte-Insulator-Semiconductor (EIS). As shown in FIG. 2, the sensing membrane consists of the a-WO$_3$ layer.

Figure 3:
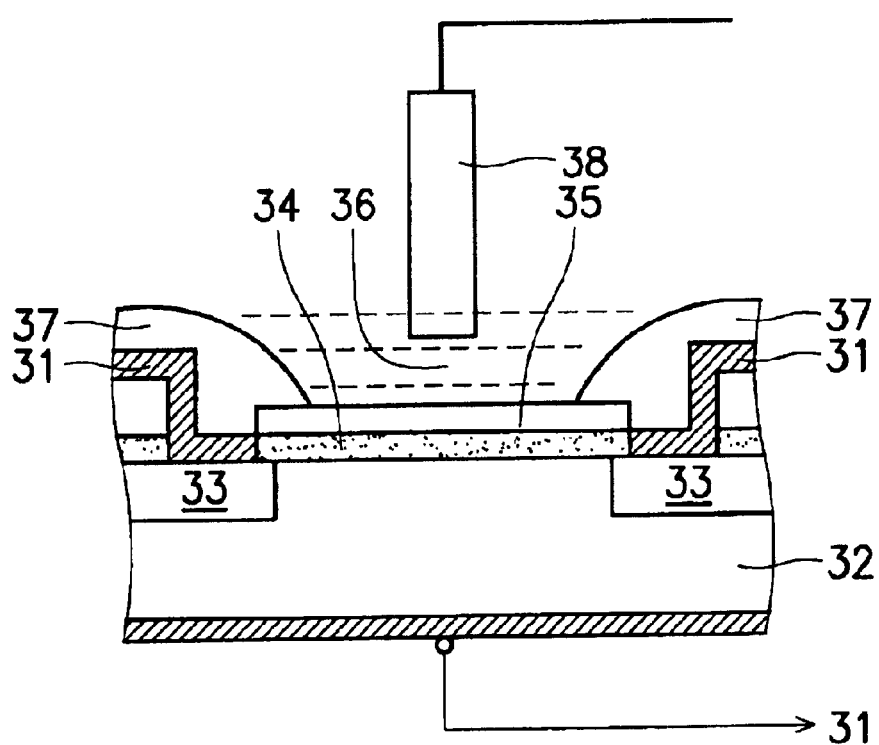
FIG. 3 is a cross-sectional view of an ISFET with a gate consisting of a-$WO_3$/$SiO_2$.

FIG. 3 shows the cross-sectional view of a RF-sputtering a-WO$_3$ ISFET according to a preferred embodiment of the present invention. The structure of this ISFET is similar to that of MOSFET. The difference between the ISFET and MOSFET is that the metal gate of the MOSFET is replaced by an a-WO$_3$ sensing membrane 35, an aqueous solution 36 and a reference electrode 38. The circuits were formed by contacting the metal wires 31, preferably consisting of Al, with source/drain 33. Since the sensing membrane 35 contacts the detected solution 36, the whole device in addition to the sensing membrane 35 must be enclosed by a sealing layer 37 consisting of a material with good insulating property, such by as epoxide resin. The reference electrode 38 was used to provide a detecting base.

The sensing membrane 35 of the ISFET is dipped into the detected solution 36 during operation, therefore the key point of the transformation from chemical equivalence to electrical equivalence within the ISFET is the contacting of the sensing membrane 35 and the aqueous solution 36. The reaction mechanism of the ionic activity within the solution is the interface potential obtained from the interface between the aqueous solution 36 and the sensing membrane 35 dipped in the aqueous solution 35. The interface potential will vary with the ionic activities of various aqueous solutions. In addition, the interface potential regulates the channel conduction of the ISFET, which will result in the change of current within the source/drain 33.

Figure 4:
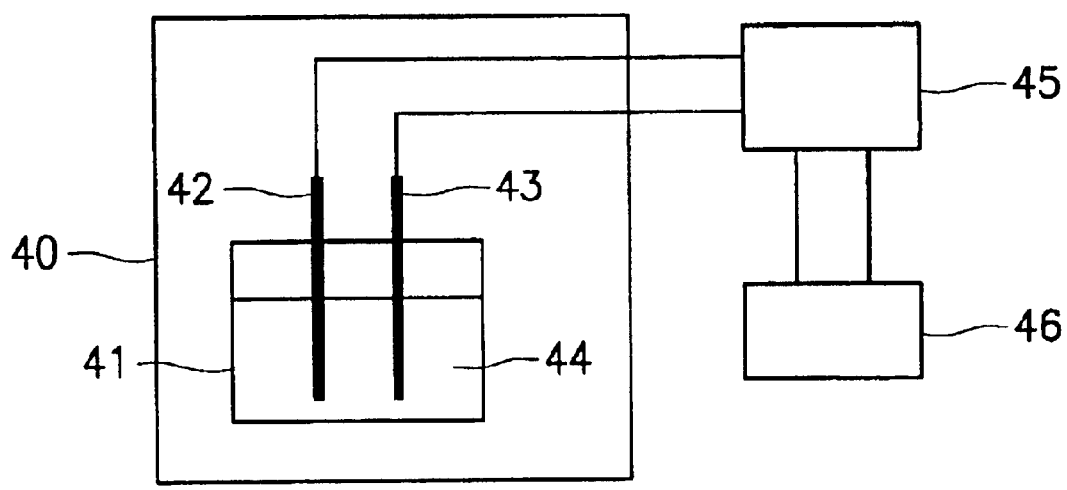
FIG. 4 is a schematic cross-sectional view of a capacitance-voltage measuring system.

FIG. 4 is the schematic cross-sectional view of the measuring system used to measure the capacitance and voltage of the device. The measurement is controlled by a computer 46 and analyzed by an inductance-capacitance-resistance analyzer 45 (HP 4284A). During measuring, the device 42 and reference electrode 43 are simultaneously put into a beaker 41 filled with aqueous solution 44. The detection is performed in a dark box 40 to reduce the effect caused by light.

Figure 5:
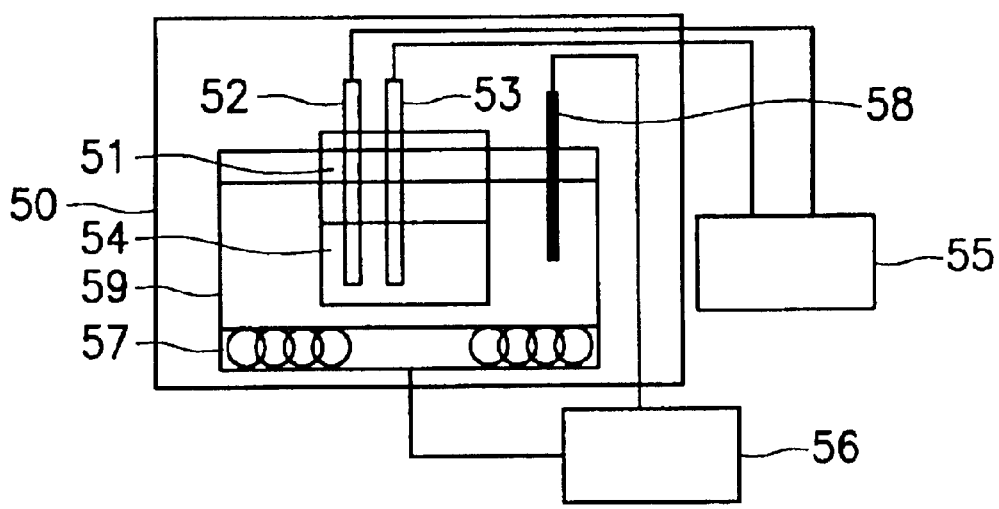
FIG. 5 is the schematic cross-sectional view of an ISFET current-voltage measuring system.

FIG. 5 shows the cross-sectional view of a current-voltage measuring system of the ISFET according to the present invention. During measuring, the temperature of the aqueous solution was maintained by a temperature maintainer consisting of a P. I. D temperature controller 56, a heater 57 and a thermal couple 58. By placing the beaker 51 filled with full detected solution 54 on the container 59 of heater 57 in the bottom of this device, the temperature of the detected solution 54 was controlled through measuring the temperature of the detected solution 54 and maintained at a constant temperature. The aqueous solution was measured at room-temperature, therefore the temperature was set at 25° C. to avoid error caused-by temperature variation. Moreover, a semiconductor parameter analyzer 55 was used to analyze the data.

Figure 6:
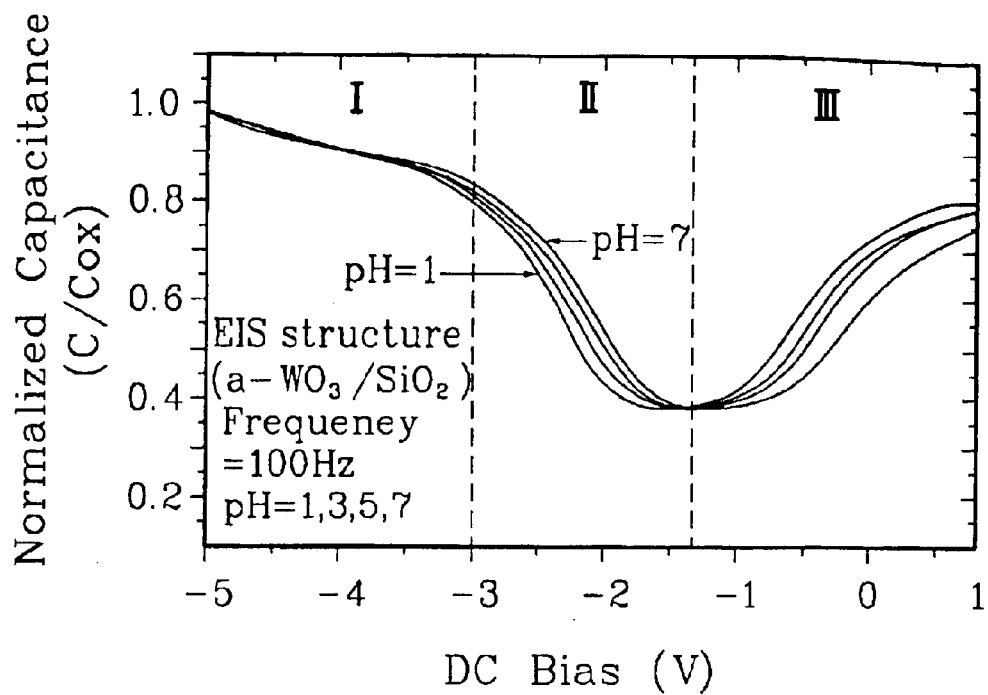
FIG. 6 shows the capacitance-voltage curves of the a-$WO_3$/$SiO_2$ gate EIS structure under various pH values (1, 3, 5, 7).

FIG. 6 shows the capacitance-voltage curves of the RF-sputtering a-WO$_3$/SiO$_2$ gate EIS Structure in acidic solution with various pH values (1, 3, 5, 7), measured by an inductance-capacitance-resistance precision analyzer (LCR Precision Analyzer, HP4284A), wherein the frequency was set at 100 Hz. As shown in FIG. 6, the capacitance-voltage curves can be divided into an accumulation region I, an flat band region II, and an inversion region III. The C–V curves adequately shifted when the pH value of the aqueous solution changed. The sensitivity was calculated by placing the EIS in aqueous solutions with various pH values and measuring the shift voltage of the flat band region II. In addition, the curves locating in the flat band region shifted linearly with the change of solution.

The main reason for the capacitance-voltage curve to rightward shift with the increasing pH value is that the increased pH value will lower the concentration of hydrogen ions, thereby the potential of the surface of the sensing membrane will be reduced. Therefore, the positive carriers within the oxide layer move to the surface of the sensing membrane. High voltage is needed to force the positive carriers to move into the inside of the oxide layer. Accordingly, the capacitance-voltage curve shifts rightward when pH value increases.

Figure 7:
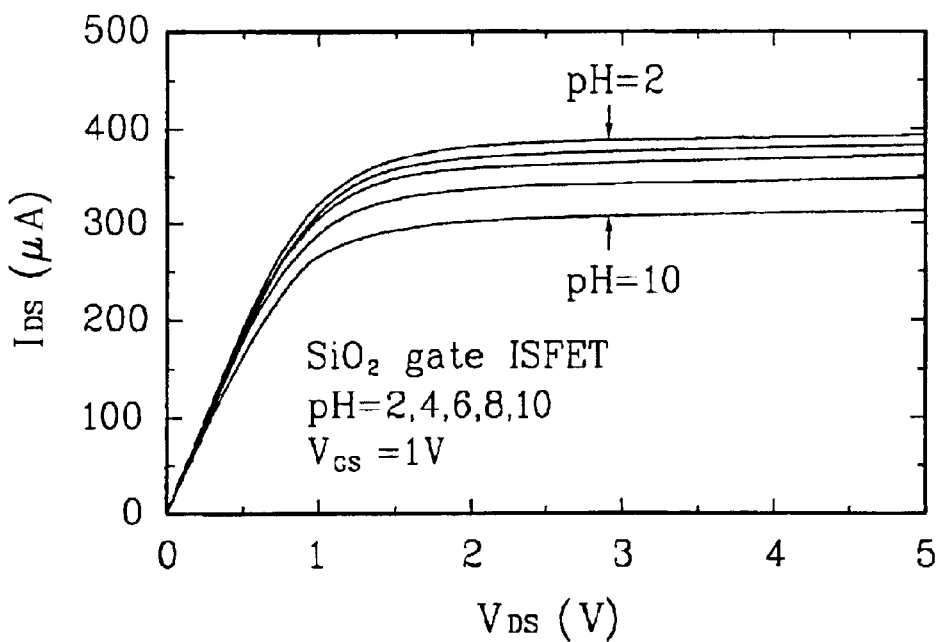
FIG. 7 shows the current-voltage curves of the $SiO_2$-gate ISFET under various pH values (2, 4, 6, 8, 10).

FIG. 7 shows the current-voltage curves of aqueous solutions with various pH values (2, 4, 6, 8, 10) measured by the single gate ISFET, using $SiO_2$ as the sensing material, under room temperature. A semiconductor parameter analyzer (Model HP 4145B) was used to analyze the data. As shown in FIG. 7, the channel current of the device decreased with the increasing pH value; that's to say, the channel current of the ISFET changed with the hydrogen ions in the aqueous solution. According to the obtained results, when the ion sensor consists of $SiO_2$, the current changes non-linearly, and the variation increases with the increasing pH value.

Figure 8:
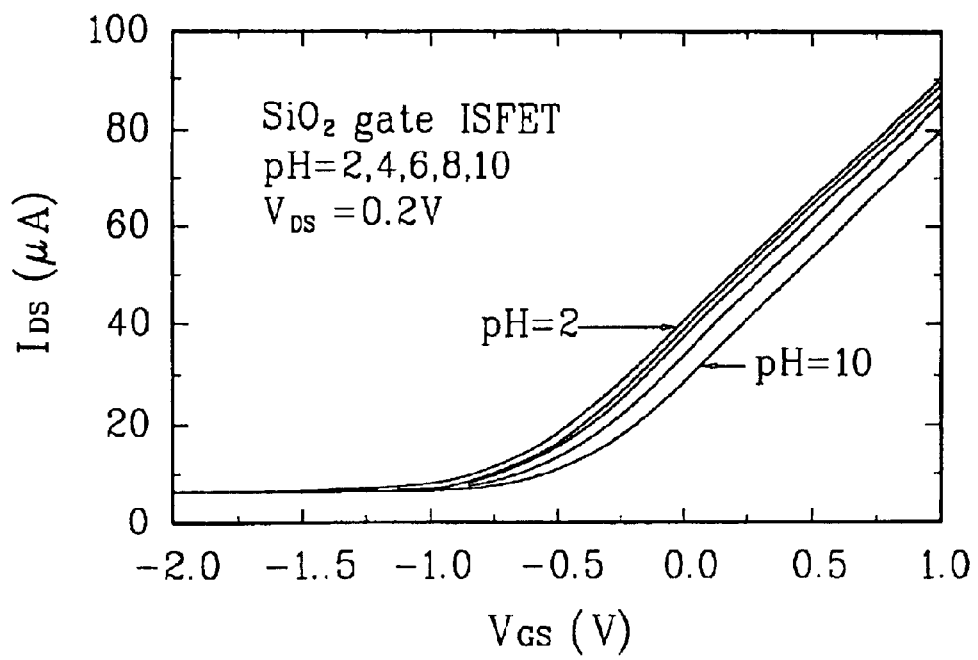
FIG. 8 shows the current-voltage curves of the $SiO_2$-gate ISFET under various pH values (2, 4, 6, 8, 10).

FIG. 8 shows the current-voltage curves of the aqueous solutions with various pH values (2, 4, 6, 8, 10) measured by the single gate ISFET, using $SiO_2$ as the sensing membrane, under room-temperature. A semiconductor parameter analyzer (Model HP 4145B) was used to analyze the obtained data. As shown in FIG. 8, the threshold voltage increased with the increasing pH value. Consequently, the variation of the threshold voltage of the ISFET (i.e. the sensitivity of the sensor; S) in aqueous solutions with various pH values can be calculated. The definition of S is:

$$S = \Delta V_{th}/\Delta pH \text{ (mV/pH)}$$

wherein, $\Delta V_{th}$ is the variation of threshold voltage of the ISFET in the solution with various pH values ($\Delta pH$).

According to the obtained results, the linearity and sensitivity of the single $SiO_2$-gated sensor were poor, wherein the average sensitivity of the single $SiO_2$ gated sensor was about 32.3 mV/pH under ranging pH=2 to pH=10.

Figure 9:
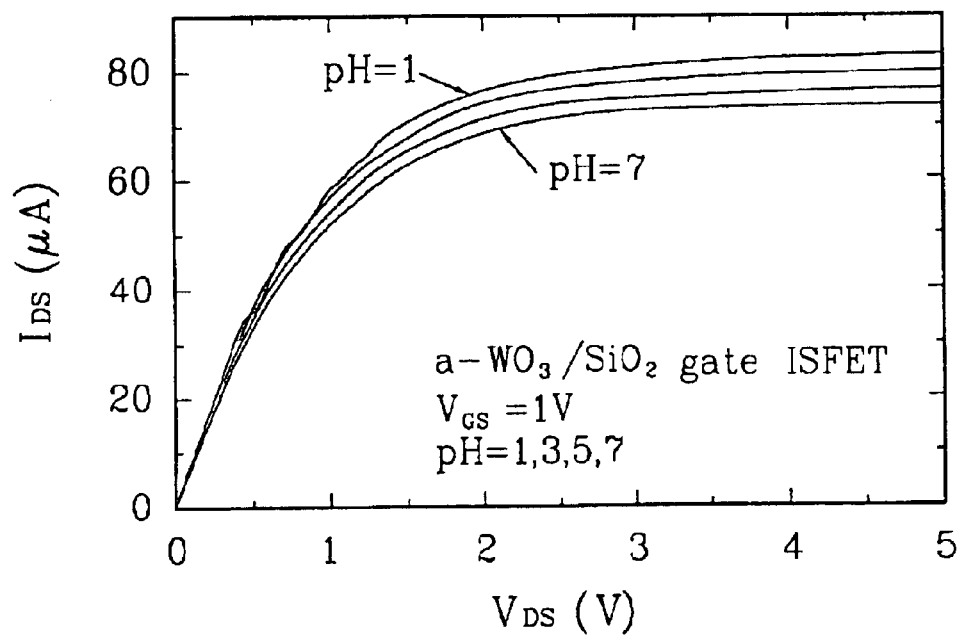
FIG. 9 shows the current-voltage curves of the a-$WO_3$/$SiO_2$ gate ISFET under various pH values (1, 3, 5, 7).

FIG. 9 shows the current-voltage curves of the RF-sputtering a-$WO_3$/$SiO_2$ gated ISFET fabricated according to this invention, wherein the measurement was accomplished by placing the sensing device in the acidic aqueous solutions (pH=1, 3, 5, 7) under room temperature. Similarly, the obtained data were analyzed by the semiconductor parameter analyzer (Model HP 4145B). According to FIG. 9, it was found that the channel current changed with the concentration of the hydrogen ions and the channel current linearly decreased with the increasing pH value of the aqueous sample when a-$WO_3$ sensing membrane was used.

Figure 10:
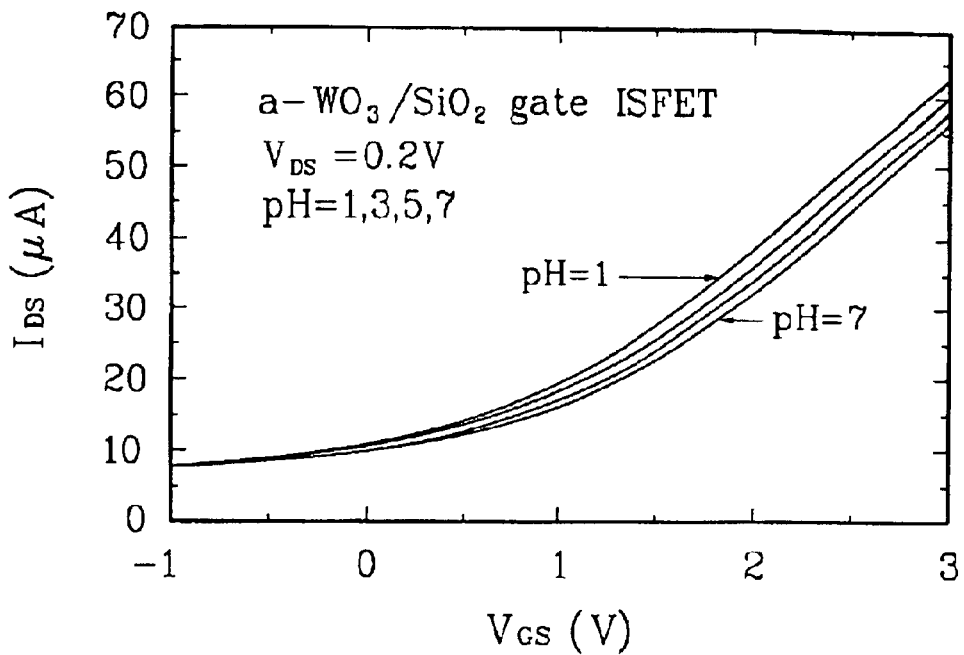
FIG. 10 shows the current-voltage curves of the a-$WO_3$/$SiO_2$ gate ISFET under various pH values (1, 3, 5, 7).

FIG. 10 shows the current-voltage curves of the RF-sputtering a-$WO_3$/$SiO_2$ gate ISFET fabricated according to this invention, wherein the measurement was accomplished by placing the sensing device in the acidic aqueous solutions (pH=1, 3, 5, 7) under room temperature. Similarly, the obtained data were analyzed by the semiconductor parameter analyzer (Model HP 4145B). According to FIG. 10, it was found that the threshold voltage linearly increased with the increasing pH value of the aqueous solution when a-$WO_3$ sensing membrane was used.

Figure 11:
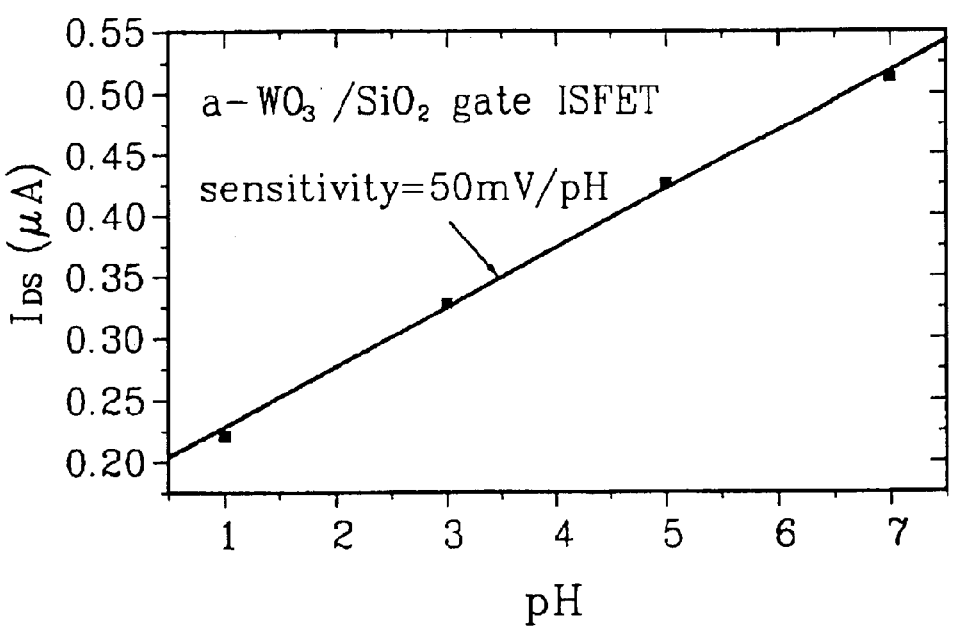
FIG. 11 shows the sensitivity of the a-$WO_3$/$SiO_2$ gate ISFET under various pH values (1, 3, 5, 7).

FIG. 11 shows the sensitivity of the a-$WO_3$/$SiO_2$ gate ISFET fabricated according to this invention under various pH values (1, 3, 5, 7). As shown in the FIG. 11, the slope of the curve demonstrated the sensitivity of the sensing device. Accordingly, the sensitivity of the sensing device consisting of a-$WO_3$/$SiO_2$ was 50 mV/pH.

Moreover, Table 1 shows the sensitivity of the a-$WO_3$/$SiO_2$-gate ISFET measured in acidic aqueous solutions (pH=1~5). As shown in Table 1, the sensitivity of the a-$WO_3$/$SiO_2$-gate ISFET measured in acidic aqueous solutions (pH=1~5) ranged from 50~58 mV/PH, and the sensitivity had no relationship to the thickness of the a-$WO_3$ sensing membrane. Thereby, the thickness of the sensing membrane will not affect the sensitivity of the sensing device.

TABLE 1

Sensitivity of the ISFET with different thickness of a-$WO_3$/$SiO_2$ gate under pH = 1~5

| Thickness (Å) | 900 | 1400 | 2050 | 2200 | 2300 | 2500 | 3100 | 3300 |
|---|---|---|---|---|---|---|---|---|
| Sensitivity (mV/pH) | 50 | 54 | 53 | 52 | 58 | 55 | 54 | 53 |

The sensitivities of a-$WO_3$/$SiO_2$-gate ISFET, $SiO_2$-gate ISFET, $Si_3N_4$/$SiO_2$-gate ISFET, $Al_2O_3$/$SiO_2$-gate and $Ta_2O_5$/$SiO_2$-gate ISFET were compared. The results were shown in Table 2. As shown in Table 2, it was noted that the sensitivity and the linearity of the double layer-gate ISFETs were higher than those of the single $SiO_2$-gate ISFET. In addition, the RF-sputtering a-$WO_3$ was superior to the above-mentioned materials on the $SiO_2$ layer when ISFET was used to detect acidic aqueous solution. The sensitivity of the a-$WO_3$/$SiO_2$-gate ISFET ranged from 50 to 58 mV/pH under pH=1~5.

TABLE 2

| Material | $SiO_2$ | $Si_3N_4$/$SiO_2$ | $Al_2O_3$/$SiO_2$ | $Ta_2O_5$/$SiO_2$ | a-$WO_3$/$SiO_2$ |
|---|---|---|---|---|---|
| Testing range (pH value) | 2~10 | 1~13 | 1~13 | 1~13 | 1~5 |
| Sensitivity (mV/pH) | 32~33 | 46~56 | 53~57 | 56~57 | 50~58 |
| Linearity | Bad | Good | Good | Good | Good |

As above-mentioned description, the advantages of the amorphous tungsten oxide ISFET according to this invention include:

1. The a-$WO_3$/$SiO_2$-gate ISFET according to this invention is formed by replacing the traditional metal layer existing in the gate of FET with a RF-sputtering a-$WO_3$ membrane. In addition to being easy to produce, other advantages include high input resistance, low output resistance, short reaction time, trace detectable, and MOS processes compatibility.
2. The gate of the ISFET is double layer consisting of a-$WO_3$/$SiO_2$, which is sensitive when used to detect an acidic aqueous solution. Accordingly, this a-$WO_3$/$SiO_2$-gate ISFET can be applied to monitor and detect the industrial effluent, and particularly acidic effluent. Since the ISFET is trace detectable, it can be used as a bio-sensor.

3. Since a-WO$_3$ is used as the material of the sensing membrane for detecting hydrogen ions, and the MOS structure is used, the H$^+$-detecting device has both the properties of MOS and excellent H$^+$-detecting ability.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claim is:

1. An α-WO$_3$ gated ISFET device, comprising:
   a semiconductor substrate;
   a gate oxide layer on the semiconductor substrate;
   an α-WO$_3$ layer formed by RF-sputtering overlying the gate oxide layer to form an α-WO$_3$ gate;
   a source/drain in the semiconductor substrate beside the α-WO$_3$ gate;
   a metal wire on the source/drain; and
   a sealing layer overlying the metal wire, and exposing the α-WO$_3$ layer.

2. The device as claimed in claim 1, wherein the length of the channel, the width of the channel and ratio of width/length of the channel of the ISFET is about 50 μm, 1000 μm, and 20 respectively.

3. The device as claimed in claim 1, wherein the semiconductor substrate is P-type.

4. The device as claimed in claim 1, wherein the resistivity of the semiconductor substrate ranges from 8 to 12 Ω·cm.

5. The device as claimed in claim 1, wherein the lattice parameter of the semiconductor is (1,0,0).

6. The device as claimed in claim 1, wherein the thickness of the gate oxide is about 1000 Å.

7. The device as claimed in claim 1, wherein the thickness of the tungsten oxide layer is at least 1000 Å.

8. The device as claimed in claim 1, wherein the metal wire consists of Al.

9. The device as claimed in claim 1, wherein the sealing layer consists of epoxide resin.

10. The device as claimed in claim 1, wherein the source/drain is N-type.

11. The device as claimed in claim 10, wherein the N-type impurities within the source/drain consist of phosphorous.

* * * * *